(12) United States Patent
Dugand et al.

(10) Patent No.: US 11,642,465 B2
(45) Date of Patent: May 9, 2023

(54) DEVICE FOR INJECTING A LIQUID PRODUCT HAVING SIMPLIFIED ASSEMBLY

(71) Applicant: NEMERA LA VERPILLÈRE, La Verpillière (FR)

(72) Inventors: Pascal Dugand, Estrablin (FR); Kevin Stamp, Sheffield (GB)

(73) Assignee: Nemera La Verpillière

( * ) Notice: Subject to any disclaimer, the term of this patent is extended or adjusted under 35 U.S.C. 154(b) by 386 days.

(21) Appl. No.: 15/999,730

(22) PCT Filed: Jan. 13, 2017

(86) PCT No.: PCT/FR2017/050077
§ 371 (c)(1),
(2) Date: Aug. 20, 2018

(87) PCT Pub. No.: WO2017/140962
PCT Pub. Date: Aug. 24, 2017

(65) Prior Publication Data
US 2019/0224416 A1      Jul. 25, 2019

(30) Foreign Application Priority Data

Feb. 19, 2016   (FR) .................................... 1651377

(51) Int. Cl.
| | |
|---|---|
| *A61M 5/24* | (2006.01) |
| *A61M 5/31* | (2006.01) |
| *A61M 5/20* | (2006.01) |
| *A61M 5/32* | (2006.01) |

(52) U.S. Cl.
CPC ............ *A61M 5/3137* (2013.01); *A61M 5/20* (2013.01); *A61M 5/2033* (2013.01); *A61M 5/3202* (2013.01); *A61M 5/3204* (2013.01); *A61M 5/326* (2013.01); *A61M 2005/206* (2013.01); *A61M 2005/3139* (2013.01); *A61M 2005/3142* (2013.01); *A61M 2205/0216* (2013.01)

(58) Field of Classification Search
CPC .. A61M 5/2033; A61M 5/326; A61M 5/3204; A61M 2005/3139; A61M 2005/3142; A61M 2005/206; A61M 2005/3261
See application file for complete search history.

(56) References Cited

U.S. PATENT DOCUMENTS

2003/0216695 A1*  11/2003  Yang .................... A61M 5/2053
                                                                604/200

FOREIGN PATENT DOCUMENTS

| WO | WO-9300949 A1 * | 1/1993 | ............ A61M 5/326 |
| WO | WO-2009081133 A1 * | 7/2009 | ............ A61M 5/326 |

* cited by examiner

*Primary Examiner* — Nathan R Price
*Assistant Examiner* — Tania Ismail
(74) *Attorney, Agent, or Firm* — St. Onge Steward Johnston & Reens LLC

(57) ABSTRACT

A part of a device for injecting a liquid product having an end sleeve and a syringe support which is able to move with respect to the end sleeve. The syringe support is designed to bear an injection syringe fitted with a removable protective cap. A deformable ring is kinematically connected to the syringe support. This ring can be deformed elastically between a configuration which is designed to axially immobilize the injection syringe in the syringe support, and a configuration designed to allow the protective cap to pass through the deformable ring.

15 Claims, 5 Drawing Sheets

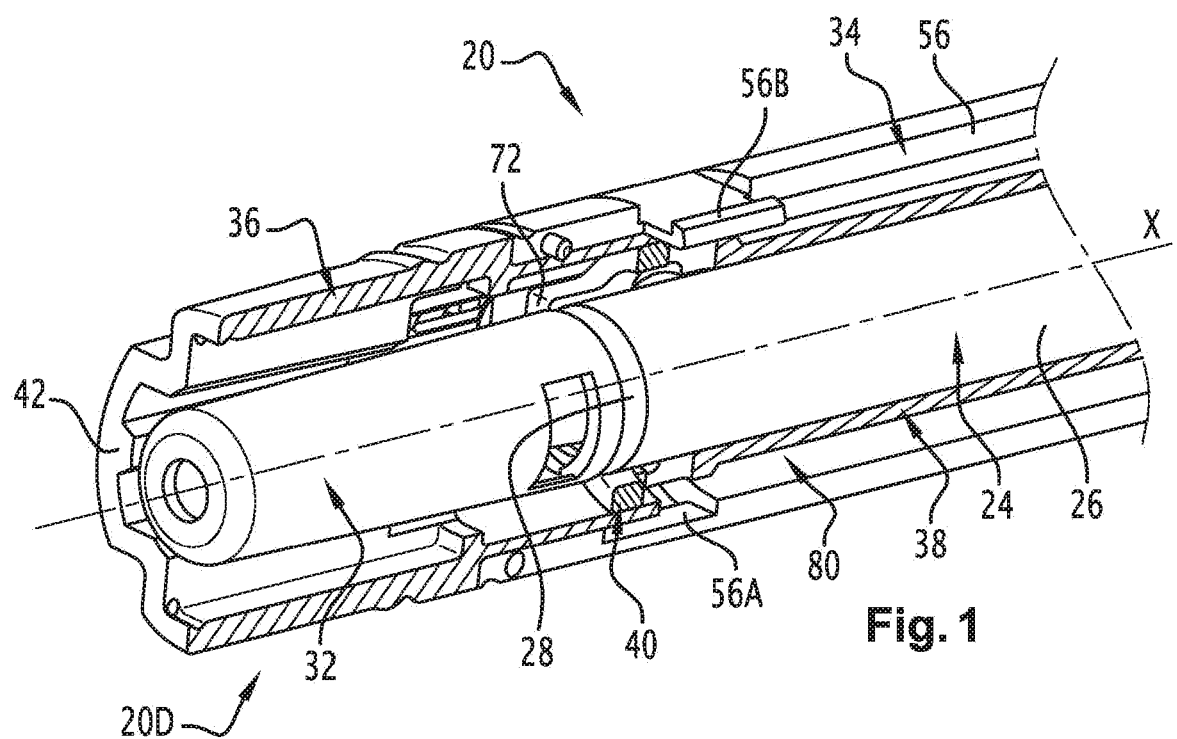
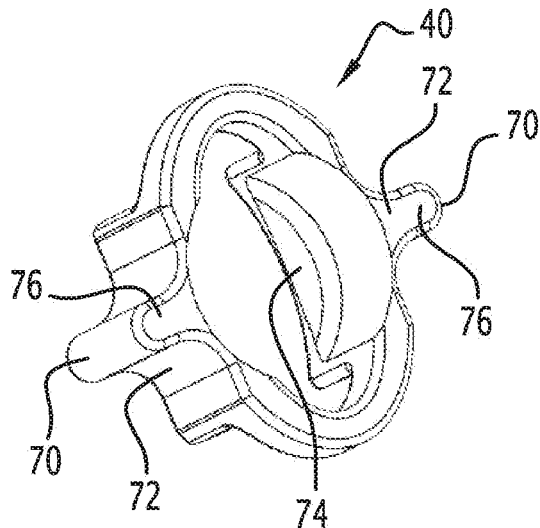
Fig. 2
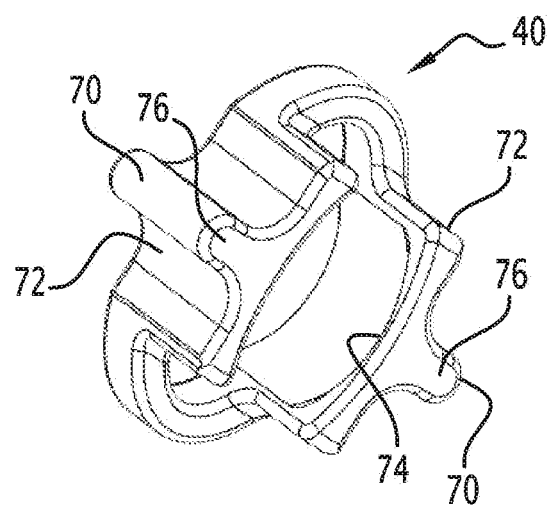
Fig. 3

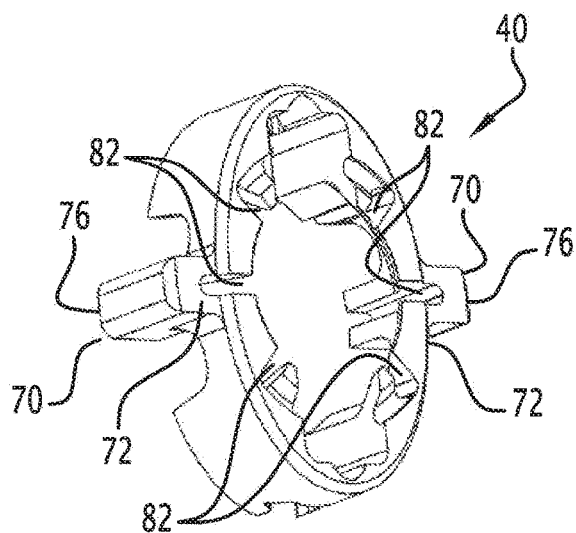
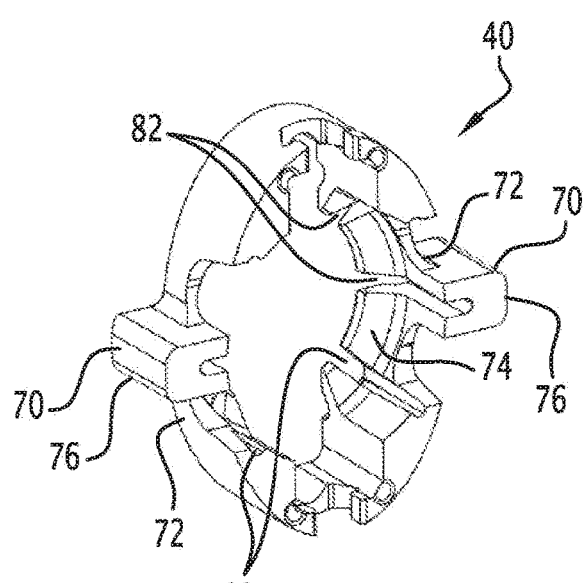
Fig. 9    Fig. 10
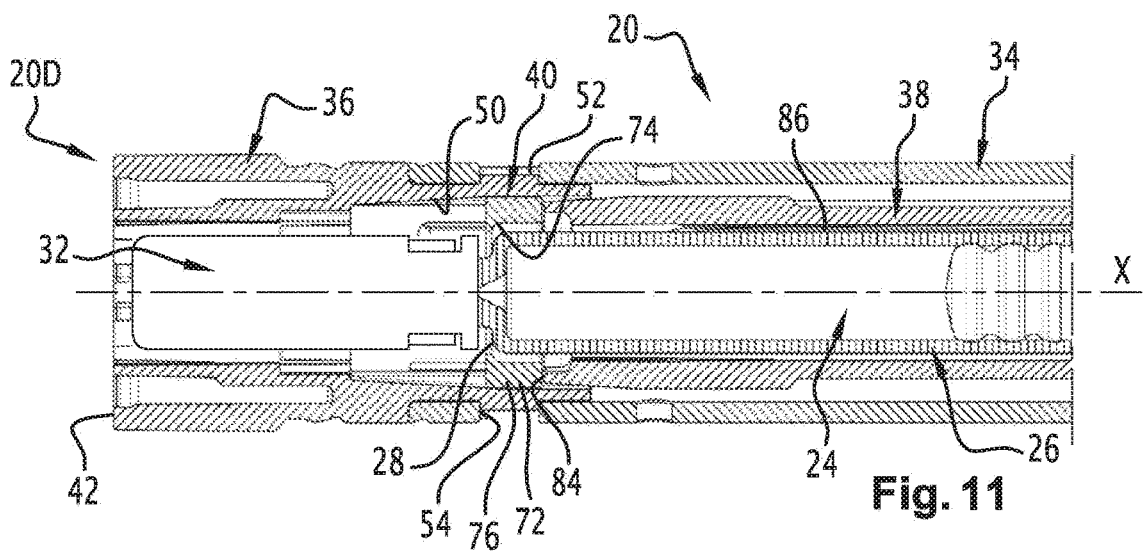
Fig. 11
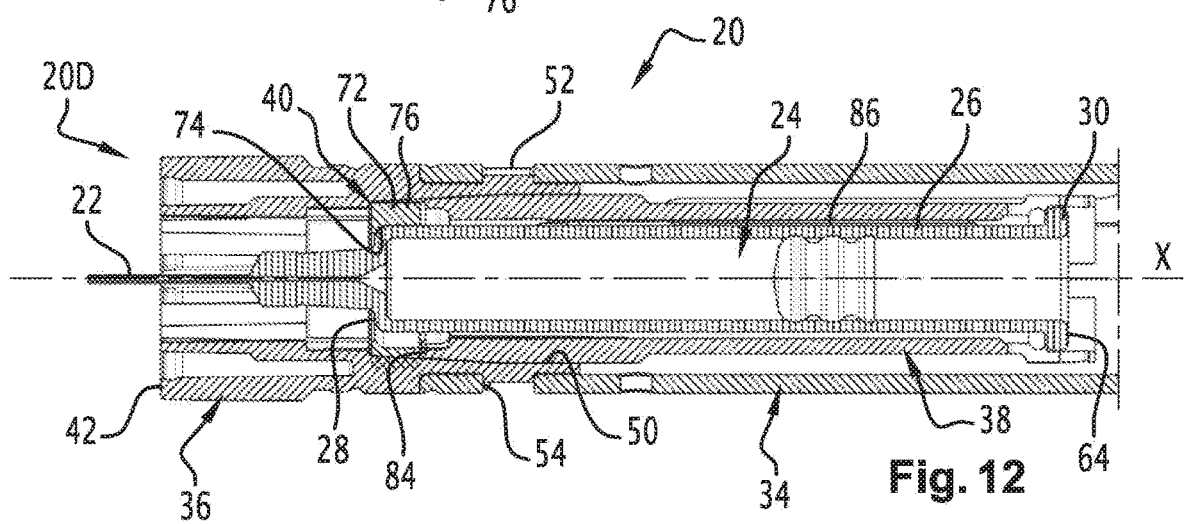
Fig. 12

DEVICE FOR INJECTING A LIQUID PRODUCT HAVING SIMPLIFIED ASSEMBLY

FIELD OF THE INVENTION

The present invention concerns the field of automatic liquid product injection devices, notably pharmaceutical liquid product injection devices.

BACKGROUND OF THE INVENTION

An automatic injection device is generally a medical device enabling the automatic administration of a liquid medication necessitating an injection. These devices in particular enable persons to inject themselves their dose of medication autonomously, for example persons suffering from rheumatoid arthritis, multiple sclerosis or diabetes or suffering an anaphylactic shock in the case of an allergy.

One example of an automatic injection device is described in the document U.S. Pat. No. 8,734,402. The device comprises an injection syringe that contains the liquid product to be injected and is fitted with a needle, and a syringe support. It generally suffices to press the device briefly onto the skin of the patient to trigger penetration of the needle into the skin, followed by injection of the liquid product, and then retraction of the needle into the interior of the device to prevent injuring a person with the needle.

SUMMARY OF THE INVENTION

To be more precise, the device comprises a syringe support configured to house the injection syringe, so that it is fixedly mounted in the syringe support throughout the operation of the device. This syringe support is formed of two semi-tubular half-shells assembled together once the injection syringe has been placed inside, so as to form a tubular shell around the syringe.

The injection syringe comprises a flange at one of its ends, and a needle protection cap, for example a rigid needle shield (RNS), at its other end. The diameter of the protection cap is often greater than that of the body of the syringe.

The syringe support in which the syringe is housed has a tubular general shape the diameter of which is close to that of the central part of the syringe; it is not always possible to insert the syringe in the syringe support after the two half-shells that constitute it have been assembled, because the flange and the cap are wider than the central part of the syringe and therefore wider than the inside diameter of the syringe support. Now the injection syringe is generally assembled into the automatic injection device by a pharmaceutical laboratory and not by the manufacturer of the automatic injection device, with the result that any simplification of the assembly of the injection syringe into the automatic injection device avoids the pharmaceutical laboratory needing to equip itself with complex apparatus.

A notable object of the invention is to provide an automatic injection device in which the assembly of the injection syringe into the automatic injection device is simplified.

To this end, the invention consists in a part of a liquid product injection device comprising:
  an end sleeve
  a syringe support mobile relative to the end sleeve, the syringe support being intended to carry an injection syringe fitted with a removable protection cap,
characterized in that it comprises a deformable ring, kinematically connected to the syringe support, this ring being elastically deformable between a configuration intended for the axial immobilization of the injection syringe in the syringe support and a configuration intended for the passage of the protection cap through the deformable ring.

Thanks to the fact that the deformable ring can be in the protection cap passage position, it is therefore possible to assemble the injection syringe carrying the protection cap in the injection device part by inserting the injection syringe axially via one end of the syringe support, the protection cap being inserted first. It is therefore no longer necessary to assemble the syringe support after positioning the injection syringe in it and it is therefore possible to assemble the two half-shells constituting the syringe support before introducing the injection syringe into it or to use a syringe support that does not consist of two half-shells.

Moreover, as in the immobilization configuration the deformable ring retains the injection syringe axially in the syringe support, the positioning and the axial retention of the injection syringe in the syringe support do not need to be effected by the flange of the injection syringe, with the result that weakening the injection syringe at the level of this flange is avoided. In fact, it is known that the spring for injecting the product can be a relatively strong spring. Now, when the injection syringe is held by its flange, the latter must retain the injection syringe when the spring exerts a pressure on the piston rod to perform the injection and when the movement of the piston is limited by the counter-pressure of the liquid product to be injected contained in the injection syringe and the friction between the piston and the inside of the body of the injection syringe. The more viscous the liquid product the greater this pressure. Also, the flange is strongly loaded during the injection, with the risk of damaging or breaking the injection syringe, in particular when the latter is made of glass. As the injection syringe is retained here by its distal end and the stresses are therefore reflected in a compression concentrated at the distal end of the injection syringe, the proximal end of the injection syringe, and therefore the flange, are spared. Note that materials such as glass are generally stronger in compression than in bending. It therefore becomes feasible to use particularly stiff springs and therefore to inject a product having a higher viscosity than heretofore. In particular, it is possible to use an injection spring producing a force in the compressed position of 20 Newtons, even 50 Newtons or 80 Newtons or more. It will be clear that it is equally feasible to use an injection syringe having no flange or for the injection syringe to take the form of a cartridge receiving the liquid product.

According to other optional features corresponding to various embodiments of the injection device part:
  at least one sector of the deformable ring, preferably two diametrically opposite sectors of the deformable ring, include an axial abutment intended to cooperate with a distal shoulder of the injection syringe when the deformable ring is in the axial immobilization configuration, the deformable ring being deformed axially between its immobilization and passage configurations by radial movement of the sector carrying the axial abutment;
  the deformable ring comprises at least one so-called deformable ring control radial projection, preferably two diametrically opposite control radial projections, carried by the sector carrying the axial abutment, this control radial projection being intended to cooperate with a complementary surface integral with the end sleeve according to the configuration to be imposed on the deformable ring;

the deformable ring is urged elastically toward its immobilization configuration, the deformable ring being deformed against its elastic return force from its immobilization configuration to its passage configuration by centrifugal radial movement of the sector carrying the axial abutment;

the control radial projection also forms a tenon for connection with the syringe support by being nested in a bracket of the syringe support forming a mortise;

the syringe support is movable relative to the end sleeve between:
  a position for mounting the injection device in which the control radial projection is radially aligned with a passage window formed in the end sleeve so as to allow the centrifugal radial movement of the sector carrying the axial abutment toward the passage configuration of the protection cap, and
  an active position of the injection device in which the control radial projection cooperates with the complementary surface integral with the end sleeve so as to prevent the centrifugal radial movement of the sector carrying the axial abutment toward the passage configuration of the protection cap;

the sector carrying the axial abutment is provided with at least one axial slot facilitating the elastic deformation of the deformable ring against its elastic return force from its immobilization configuration to its passage configuration by centrifugal radial movement of the sector carrying the axial abutment;

the deformable ring is urged elastically toward its passage configuration, the deformable ring being deformed against its elastic return force from its passage configuration to its immobilization configuration by centripetal radial movement of the sector carrying the axial abutment;

the syringe support is movable relative to the end sleeve between:
  a position awaiting the injection device in which the deformable ring is in its passage configuration, and
  an active position of the injection device in which the deformable ring is in its configuration for the axial immobilization of the injection syringe in the syringe support, the control radial projection cooperating, from the waiting position to the active position of the injection device, with the complementary surface of the end sleeve, this complementary surface forming a ramp causing the centripetal radial movement of the sector carrying the axial abutment toward the configuration for immobilization of the deformable ring;

the deformable ring is essentially made of polymer material.

The invention also consists in an injection device comprising interconnected distal and proximal parts, characterized in that the distal part comprises a part as described above.

BRIEF DESCRIPTION OF THE DRAWINGS

The invention will be better understood on reading the following description given by way of example only and with reference to the appended drawings, in which:

FIG. 1 is a perspective view partly in axial section of a device in accordance with a first embodiment of the invention for injecting a liquid product;

FIGS. 2 and 3 are perspective views, from two different points of view, of an elastically deformable ring of the injection device shown in FIG. 1;

FIGS. 9 and 10 are perspective views, from two different points of view, of a variant embodiment of the elastically deformable ring shown in FIGS. 2 and 3;

FIG. 11 is a sectional view on a plane similar to that from FIG. 4 of an injection device in accordance with a second embodiment of the invention, the deformable ring being in a cap passage configuration;

FIG. 12 is a view similar to that of FIG. 11, in which the cap has been removed and the injection device is in a configuration after insertion of the needle of the injection syringe into the skin of a patient;

DETAILED DESCRIPTION OF THE INVENTION

Figure 4:
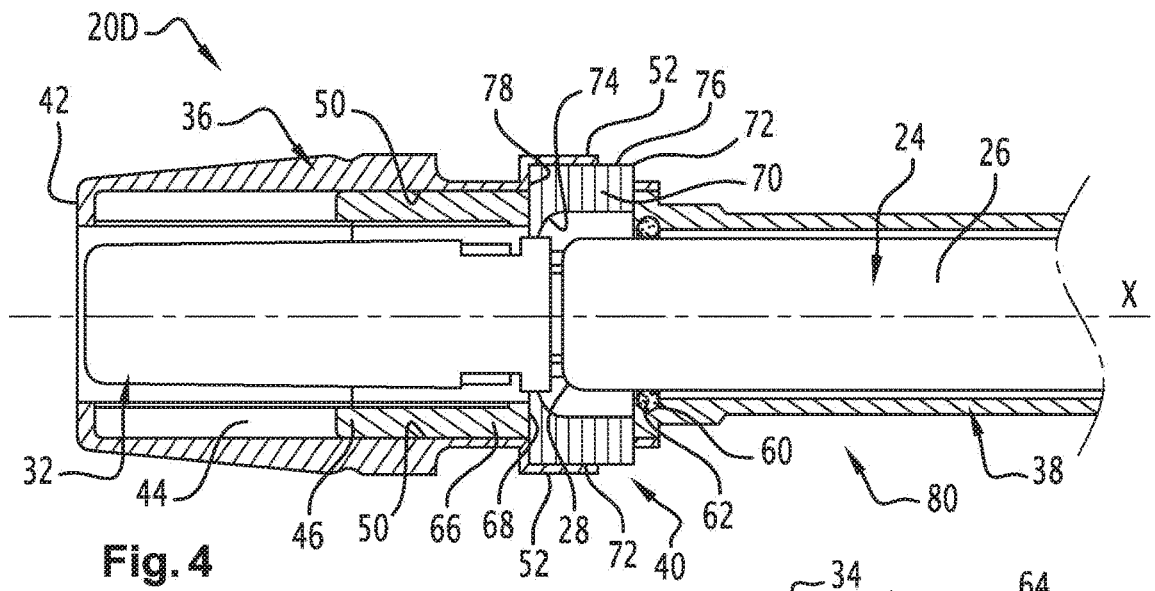
FIG. 4 is a view of a part of the injection device shown in FIG. 1 in partial section on a plane perpendicular to the section plane of FIG. 1, the deformable ring being in a cap passage configuration.

There is shown in FIGS. 1 to 10 a device 20 in accordance with a first embodiment of the invention for injecting a liquid product. To be more precise, the injection device 20 is a medical device enabling the automatic administration of a liquid medication by injection.

Thus the injection device 20 is used to administer a liquid product to a patient, more particularly a pharmaceutical product administered by injection. This injection device 20 essentially has a cylindrical general shape with axis X. To perform an injection, the patient grasps the injection device 20 by one end and applies the other end of this injection device 20 against their skin. A series of movements of various members of the injection device 20 that are controlled automatically then leads to the insertion of an injection needle 22 of an injection syringe 24 into the skin of the patient and then the injection of its content through the injection needle 22.

Hereinafter, by proximal is meant an element of the injection device 20 near the hand of the patient and by distal is meant an element of the injection device 20 far from the hand of the patient. Consequently the end of the injection device 20 that the patient applies against their skin is a distal end of the injection device 20.

As can be seen, for example in FIGS. 1 to 5, the injection syringe 24 includes a syringe body 26 of globally tubular shape around the axis X. The syringe body 26 carries the injection needle 22 (visible in FIG. 5) at its distal end. The syringe body 26 includes a distal shoulder 28 near the injection needle 22. The proximal end of the syringe body 26 comprises a flange 30 (visible in FIG. 5). A piston (not visible in FIGS. 1 to 10 showing the first embodiment but visible in FIGS. 11 and 12 showing the second embodiment) is slidably mounted in the syringe body 26 and enables the injection of a liquid product contained in the syringe body 26 via the injection needle 22 when it is moved toward the distal end of the syringe body 26.

The injection syringe 24 is, in this example, a pre-filled glass syringe, with stuck-on needle, having a capacity of 1 ml (milliliter). It will be noted that the syringe body 26 defines a maximum liquid capacity volume, but that it is feasible to fill it only partly, by advancing the piston toward the distal end of the syringe body 26.

FIG. 1 shows a distal part 20D of the injection device 20 housing the injection syringe 24, fitted with a removable protection cap 32 covering the injection needle 22. This distal part 20D comprises various members transmitting movements and forces produced by other members situated in a proximal part of the injection device 20 the operation of which is known to the person skilled in the art. Only one element 34 of the proximal part of the injection device 20 is shown in the figures.

Figure 5:
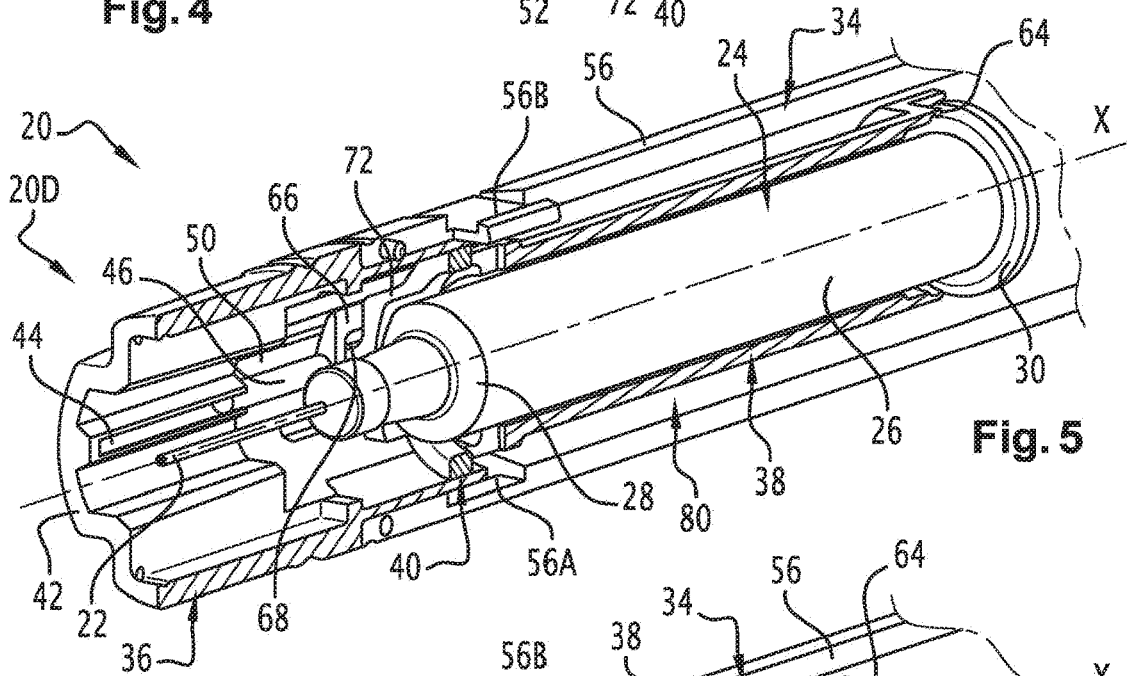
FIGS. 5 and 6 are views similar to FIG. 1, the removable cap having been removed, these figures respectively showing the injection device in configurations before and after insertion of the needle of the injection syringe into the skin of a patient.
Figure 6:
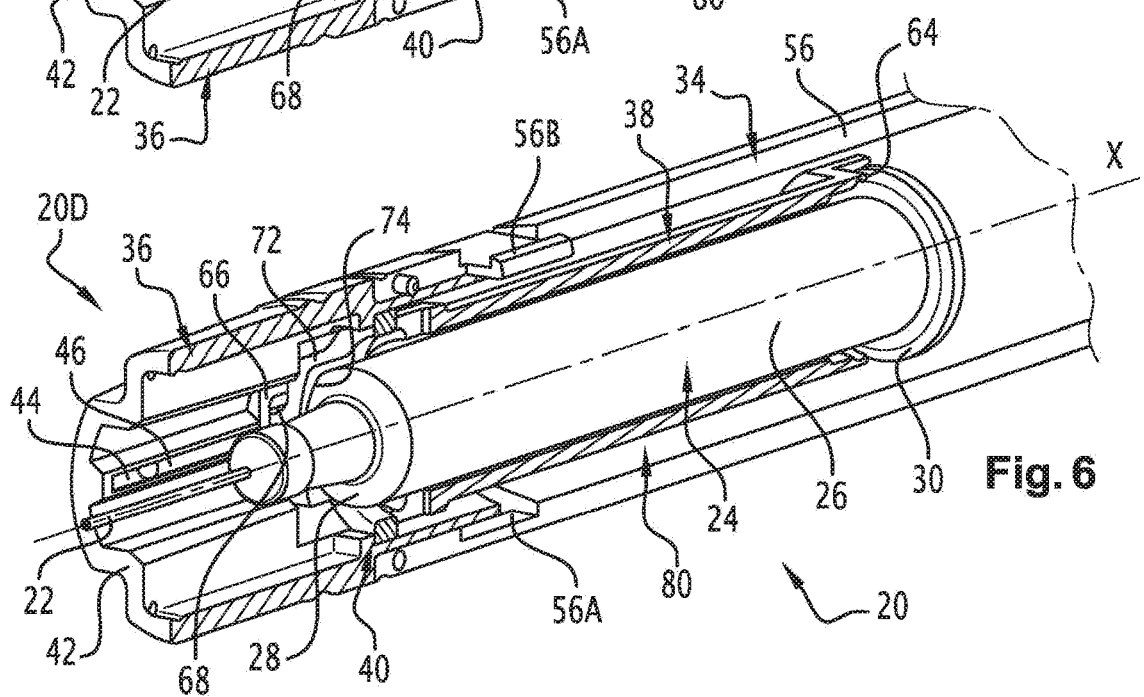

The distal part 20D of the injection device 20 comprises an end sleeve 36 relative to which a syringe support 38 is slidably mounted (see in particular FIGS. 4 to 6). Before use of the injection device 20, sliding of the end sleeve 36 relative to the syringe support 38 is prevented by a removable locking element, not shown, housed in the end sleeve 36 and against which the syringe support 38 comes to bear. The injection syringe 24 is housed in the syringe support 38. The distal part 20D of the injection device 20 also comprises a deformable ring 40, shown in more detail in FIGS. 2 and 3, kinematically connected to the syringe support 38. The deformable ring 40 is therefore mobile relative to the end sleeve 36. This ring 40 is elastically deformable between a configuration intended for axial immobilization of the injection syringe 24 in the syringe support 38 and a configuration intended for the passage of the protection cap 32 through the deformable ring 40.

The end sleeve 36 is of essentially tubular shape with axis X. Its most distal surface 42 is intended to be brought into contact with the skin of the patient during the injection, after removal of the locking element. Two rectilinear grooves 44 of at least partly circular section (see FIGS. 5 and 6), with axes parallel to the axis X, are formed in the end sleeve 36. The interior surface of the end sleeve 36 comprises two parts, termed complementary surfaces 50 (see FIG. 4), intended to cooperate with the deformable ring 40. One function of this end sleeve 36 is to protect the injection needle 22 against any unintentional contact with an element of its environment after withdrawal of the protection cap 32 when the injection device 20 has not been activated, in particular to prevent the user unintentionally pricking themselves with the injection needle 22.

The element 34 of the proximal part shown in particular in FIGS. 1 and 4 is a member 34 connecting the proximal part with the distal part 20D of the injection device 20. This connecting member 34 is globally tubular with axis X and assembled to the end sleeve 36 by means comprising at least one lug 52 (see FIG. 4) carried by the end sleeve 36 intended to cooperate with a locking window of the connecting member 34. This locking window is not shown for the first embodiment but bears the reference 54 in FIGS. 11 and 12 showing the second embodiment.

The connecting member 34 comprises two half-shells 56 assembled to one another by clipping means comprising various notches 56A and lugs 56B. The end sleeve 36 and the connecting member 34 (see FIG. 5), after they have been assembled, remain fixed to one another throughout the operation of the injection device 20.

Figure 7:
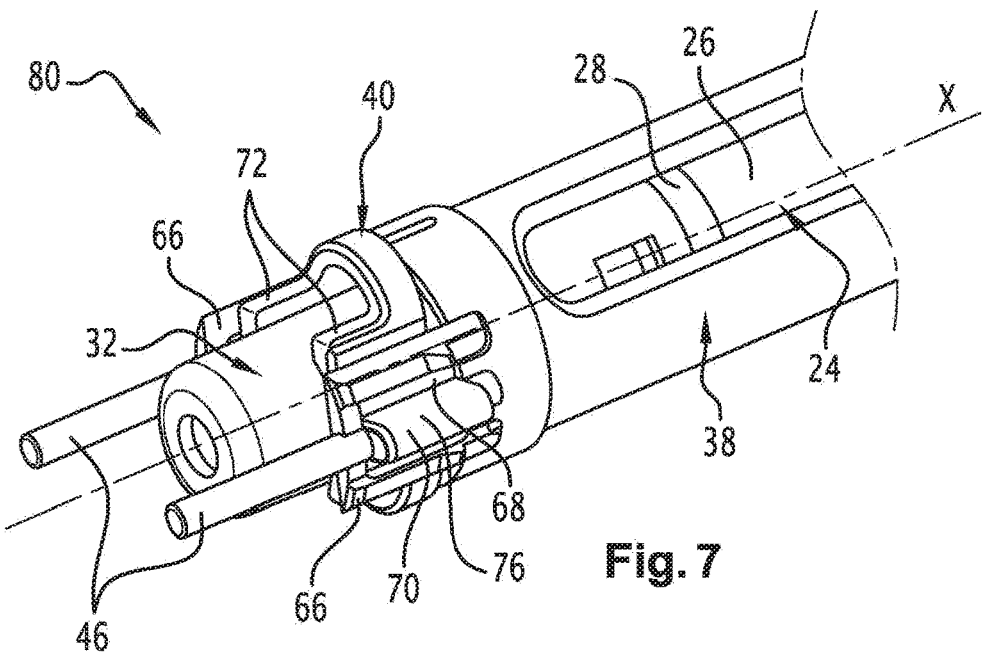
FIGS. 7 and 8 are perspective views of a part of the injection device from FIG. 1, the deformable ring being respectively in its cap passage and syringe axial immobilization configurations.

The syringe support 38 is a member of tubular shape with axis X and is open at its two ends. The distal end 38D of the syringe support 38 is provided with two cylindrical rods 58, shown in particular in FIGS. 4 and 5, intended to cooperate with the two grooves 44 of the end sleeve 36 to guide the syringe support 38 in its movement in translation relative to the end sleeve 36. The distal part of the syringe support 38 includes a distal housing 60 intended to receive an elastic ring 62 shown in FIG. 4. This elastic ring 62 enables the syringe body 26 to be centered in the syringe support 38 with no risk of breaking the injection syringe 24 and, on activation of the injection device 20, axially retains the syringe body 26 in the syringe support 38 so that the movement in translation of the syringe support 38 leads to the movement in translation of the syringe body 26 to insert the injection needle 22 into the body. However, this elastic ring 62 cannot provide the axial locking of the syringe body 26 in the syringe support 38 during the injection. At its distal end, the syringe support 38 includes a proximal spot facing 64 (see FIGS. 5 and 6) intended to receive the flange 30 of the syringe body 26. It should be noted that the contact of this proximal spot facing 64 with this flange 30 does not serve as an abutment in the axial immobilization of the injection syringe 24 in the syringe support 38 during operation of the injection device 20. In fact, on operation of the injection device 20, the flange 30 of the injection syringe 24 is not subjected to the axial forces linked to the axial force exerted on the piston. As can be seen in FIGS. 4 and 7, the distal part of the syringe support 38 includes two brackets 66 forming two mortises 68 intended to receive connecting tenons 70 of the deformable ring 40. The deformable ring 40 is therefore kinematically connected to the syringe support 38. The syringe support 38 is assembled with the end sleeve 36 by means not shown in the figures, known to the person skilled in the art, enabling the axial movement with axis X of the syringe support 38 relative to the end sleeve 36 after removal of the locking element.

The deformable ring 40 is essentially made from polymer material and is intended to cooperate axially with the injection syringe 24. Referring to FIGS. 2 and 3 it is seen that the deformable ring 40 comprises at least one sector, preferably two diametrically opposite sectors 72. The sectors 72 include axial abutments 74 each intended to cooperate with the distal shoulder 28 of the injection syringe 24. The deformable ring 40 comprises at least one, preferably two diametrically opposite, so-called control radial projections 76 on the deformable ring 40. These control radial projections 76 form the tenons 70 for connection to the syringe support 38 and are carried by the sectors 72 carrying the axial abutments 74. These control radial projections 76 are intended to cooperate with the complementary surfaces 50 carried by the end sleeve 36. As specified above, the deformable ring 40 can be deformed between a configuration intended to immobilize the injection syringe 24 and a configuration intended for the passage of the protection cap 32. The passage from one configuration of the deformable ring 40 to the other is effected by radial movement of the sectors 72 carrying the axial abutments 74. For these sectors 72, reference will be made to a protection cap 32 passage configuration and an injection syringe 24 axial immobilization configuration when the positions of the sector 72 are imposed by the corresponding configurations of the deformable ring 40.

Figure 8:
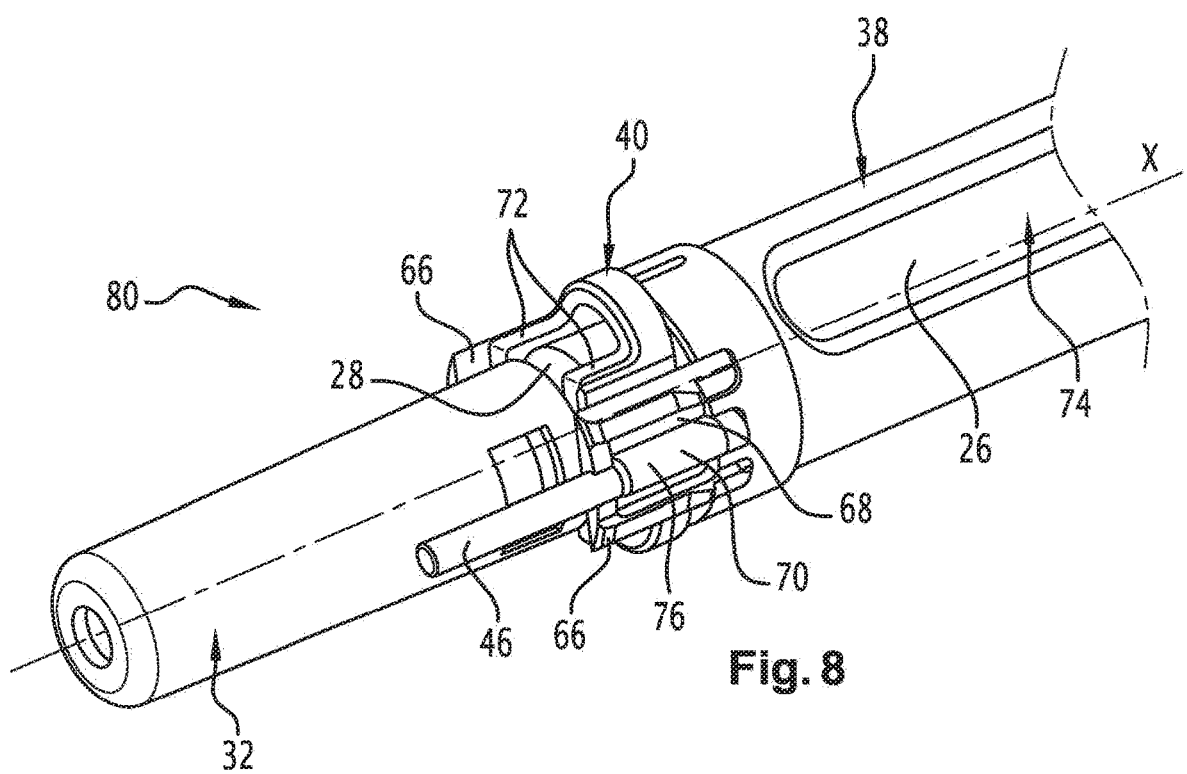
Figure 13:
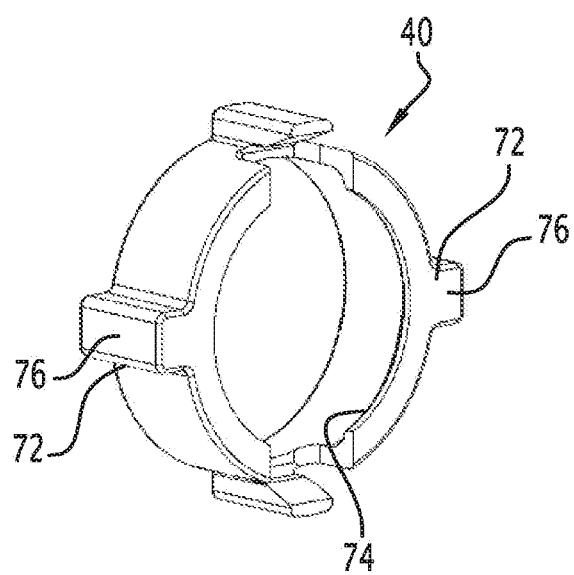
FIGS. 13 and 14 are perspective views, from two different points of view, of an elastically deformable ring of the injection device shown in FIG. 11.
Figure 14:
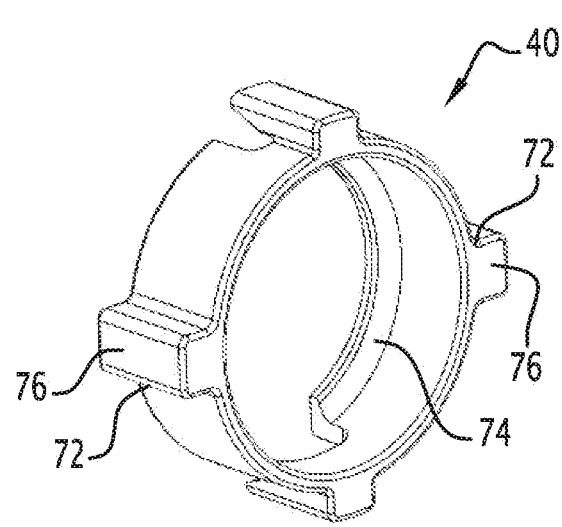

When the deformable ring 40 is mounted in the syringe support 38, the two control radial projections 76 are nested in the mortises 68 formed by the brackets 66 of the syringe support 38 (see in particular FIG. 8). The deformable ring 40 and the syringe support 38 are therefore connected to one another in their movement in translation along the axis X.

When the deformable ring 40 is not loaded, it is returned elastically to its configuration for axially immobilizing the injection syringe 24 in the syringe support 38. In this configuration, the space between the two axial abutments 74 is sufficiently small to prevent the injection syringe 24 from passing through the deformable ring 40. Also in this configuration, the axial abutments 74 cooperate with the distal shoulder 28 of the syringe body 26 and absorb the axial forces in the distal direction applied to the injection syringe 24. The injection syringe 24 is therefore immobilized axially in a sufficient manner to absorb the force of the injection spring, even during the injection of viscous products, without the injection syringe 24 moving axially and without the flange 30 having to absorb forces with the attendant risk of damaging it.

When centrifugal forces are applied to the two sectors 72 of the deformable ring 40, the deformable ring 40 is deformed, against its return force, so that the two sectors 72 carrying the control radial abutments 76 are moved radially from their immobilization configuration toward their protection cap 32 passage configuration. When the deformable ring 40 is in the protection cap 32 passage configuration, the axial abutments 74 are farther apart than when the deformable ring 40 is in the immobilization configuration so as to allow a sufficient free passage for the protection cap 32 to pass through the deformable ring 40.

To assemble the injection device 20, the injection syringe 24 is first mounted in the distal part 20D when this distal part 20D is separated from the proximal part of the injection device 20.

To mount the injection syringe 24 in the distal part 20D of the injection device 20, this injection syringe 24 is inserted in the syringe support 38 via the proximal end of the syringe support 38, the protection cap 32 passing first through this proximal end. When the protection cap 32 comes into contact with the deformable ring 40, which is then in the immobilization configuration, the proximal part of the protection cap 32 cooperates with the deformable ring 40 and applies centrifugal forces to the two sectors 72 of the deformable ring 40. The deformable ring 40 is therefore deformed into the protection cap 32 passage configuration and allows the protection cap 32 to pass. This deformation is possible because the control radial projections 76 of the deformable ring 40 are aligned with the windows 78 for passage of the control radial projections 76 (visible in FIG. 4) carried by the end sleeve 36. After the complete passage of the protection cap 32 through the deformable ring 40, the protection cap 32 no longer cooperates with the deformable ring 40, and the latter therefore returns by virtue of its elasticity into its immobilization configuration.

After having mounted the injection syringe 20 in the distal part 20D this distal part 20D is assembled with the proximal part of the injection device 20. To effect this assembly, the assembly comprising the end sleeve 36 and the injection syringe 24 is inserted in the proximal part of the injection device 20 so that the lug 52 carried by the end sleeve 36 and the locking window 54 carried by the connecting member 34 cooperate and are assembled.

Before activation, the locking element is removed from the end sleeve 36, which allows relative movement in translation between the syringe support 38 and the end sleeve 36.

When the injection device 20 is activated, a mobile part 80 of the injection device 20, including the injection syringe 24, the syringe support 38 and the deformable ring 40, is moved relative to the end sleeve 36 from a waiting or mounting position to an active position of the injection device 20. The mounting position corresponds to the waiting position before the distal part 20D and the proximal part of the injection device 20 are assembled.

When the mobile part 80 is in the mounting position, the control radial projections 76 are radially aligned with the windows 78 for the passage of the control radial projections 76 provided in the end sleeve 36 so as to allow the centrifugal radial movement of the sectors 72 carrying the axial abutments 74 to the protection cap 32 passage configuration. In this position the injection needle 22 is protected by the end sleeve 36, i.e. the injection needle 22 does not project axially from this end sleeve 36.

On its movement relative to the end sleeve 36 from the waiting position to the active position, the mobile part 80 advances along the axis X in the proximal to distal direction. The injection needle 22 therefore advances toward the skin of the patient and then pierces it and thus penetrates into the body of the patient. During this movement, the control radial projections 76 and the window 78 for passage of the control radial projections 76 of the end sleeve 36 are out of alignment. The control radial projections 76 then each cooperate with the corresponding complementary surface 50 of the end sleeve 36 so as to prevent centrifugal radial movement of the sectors 72 carrying the axial abutments 74 to the protection cap 32 passage configuration.

When the injection device 20 is in the active position, the deformable ring 40 is therefore no longer able to deform toward its passage configuration, the injection syringe 24 then being immobilized axially by the axial abutments 74 of the sectors 72 of the deformable ring 40.

In a variant shown in FIGS. 9 and 10, the deformable ring 40 has at least one axial slot 82, preferably a plurality of axial slots 82. The purpose of these axial slots 82 is to facilitate the deformation of the deformable ring 40 against its return force from its immobilization configuration to its passage configuration by centrifugal radial movement of the sector 72 carrying the axial abutments 74. Some of the sectors of the deformable ring 40 delimited by the axial slots 82 can be thin to have a lower resistance to elastic deformation and therefore are easily deformed on the passage of the protection cap 32. Other sectors of the deformable ring 40 can have a thickness greater than that of the thin sectors, enabling them to form effective axial abutments 74.

In this first embodiment, the deformable ring 40 goes from its configuration intended for the passage of the protection cap 32 through the deformable ring 40 to its configuration intended for the axial immobilization of the injection syringe 24 in the syringe support 38 during the assembly of the syringe body 26 carrying the protection cap 32 in the syringe support 38.

There will be described below, with reference to FIGS. 11 to 15, a distal part 20D of an injection device 20 in accordance with a second embodiment of the invention. In this case, elements analogous to those of the preceding figures are designated by identical references.

In this embodiment, the elastic ring 62 is replaced by strips 86 fixed against the interior wall of the syringe support 38, for example made from TPE. These strips 86 have the same function as the elastic ring 62.

In contrast to the preceding embodiment, in this embodiment, the deformable ring 40 is urged elastically toward its cap passage configuration when it is not loaded. Moreover, the deformable ring 40 simply bears against the distal end of the syringe support 38. This enables the deformable ring 40 to be kinetically connected to the syringe support 38.

In fact, the deformable ring 40 is deformed from its protection cap 32 passage configuration to its injection syringe 24 axial immobilization configuration against its return force by centripetal radial movement of the sectors 72 carrying the axial abutments 74.

The deformable ring 40 goes from its protection cap 32 passage configuration to its injection syringe 24 immobilization configuration by cooperation with the complementary surfaces 50. This change of configuration is effected when the syringe support 38 slides in the end sleeve 36 from a waiting position to an active position. The complementary surfaces 50 carried by the end sleeve 36 form ramps 50 the distal parts of which are nearer the axis X than the proximal parts. When the syringe support 38 is in the waiting position, the distances between the ramps 50 and the axis X are sufficiently great for the deformable ring 40 not to be deformed and therefore to remain in the passage configuration. When the syringe support 38 is moved toward its active position, the control radial projections 76 cooperate with the ramps 50, causing the centripetal radial movement of each sector 72 carrying an axial abutment 74. The deformable ring 40 is then deformed radially toward its configuration for axial immobilization of the injection syringe 24 in the syringe support 38.

In this second embodiment, the deformable ring 40 therefore goes from its configuration intended for the passage of the protection cap 32 through the deformable ring 40 to its configuration intended for the axial immobilization of the injection syringe 24 in the syringe support 38 after activation of the injection device 20, during the phase of insertion of the injection needle 22 in the body.

It should be noted that in this second embodiment the deformable ring 40 is not mounted in mortises carried by the syringe support 38. The deformable ring 40 is simply inserted in the end sleeve 36 and is in contact with a distal annular edge 84 of the syringe support 38 (see FIGS. 11 and 12). When the mobile part 80 moves from its waiting position to its active position, the syringe support 38 pushes the deformable ring 40 axially. The deformable ring 40 and the syringe support 38 are then connected to one another in translation.

In this second embodiment, the assembly of the proximal part 20D and the distal part of the injection device 20 and of the injection syringe 2 is similar to that described for the first embodiment.

The invention is not limited to the embodiments shown and other embodiments will be clearly apparent to the person skilled in the art. It is in particular possible to provide windows for the passage of the radial projections in the connecting member, so that the deformable ring can always be deformed toward its cap passage configuration when the device is completely assembled.

The invention claimed is:

1. A part of a liquid product injection device comprising:
    an end sleeve,
    a syringe support mobile relative to the end sleeve, the syringe support being intended to carry an injection syringe fitted with a removable protection cap, and
    a deformable ring kinematically connected to the syringe support such that a movement of the syringe support is linked with a movement of the deformable ring, the deformable ring being mobile axially relative to the end sleeve and being elastically deformable between a configuration intended for the axial immobilization of the injection syringe in the syringe support during the injection and a configuration intended for the passage of the protection cap through the deformable ring;
    wherein the deformable ring comprises at least one radial projection of control of the deformable ring, the radial projection of control configured to cooperate by contact with a complementary surface integral with the end sleeve according to the configuration intended for the axial immobilization of the injection syringe in the syringe support during the injection and the configuration intended for the passage of the protection cap through the deformable ring.

2. The part according to claim 1, in which at least one sector of the deformable ring includes an axial abutment intended to cooperate with a distal shoulder of the injection syringe when the deformable ring is in the axial immobilization configuration, the deformable ring being deformed axially between its immobilization and passage configurations by radial movement of the sector carrying the axial abutment.

3. The part according to claim 2, wherein the at least one radial projection of control of the deformable ring is carried by the sector carrying the axial abutment.

4. The part according to claim 3, in which the deformable ring is urged elastically toward its immobilization configuration, the deformable ring being deformed against its elastic return force from its immobilization configuration to its passage configuration by centrifugal radial movement of the sector carrying the axial abutment.

5. The part according to claim 4, in which the at least one radial projection of control of the deformable ring also forms a tenon for connection with the syringe support by being nested in a bracket of the syringe support forming a mortise.

6. The part according to claim 4, in which the syringe support is movable relative to the end sleeve between:
    a position for mounting the injection device in which the at least one radial projection of control of the deformable ring is radially aligned with a passage window formed in the end sleeve so as to allow the centrifugal radial movement of the sector carrying the axial abutment toward the passage configuration of the protection cap, and
    an active position of the injection device in which the at least one radial projection of control of the deformable ring cooperates with the complementary surface integral with the end sleeve so as to prevent the centrifugal radial movement of the sector carrying the axial abutment toward the passage configuration of the protection cap.

7. The part according to claim 2, in which the deformable ring is urged elastically toward its immobilization configuration, the deformable ring being deformed against its elastic return force from its immobilization configuration to its passage configuration by centrifugal radial movement of the sector carrying the axial abutment, and the sector carrying the axial abutment is provided with at least one axial slot facilitating the elastic deformation of the deformable ring against its elastic return force from its immobilization configuration to its passage configuration by centrifugal radial movement of the sector carrying the axial abutment.

8. The part according to claim 3, in which the deformable ring is urged elastically toward its passage configuration, the deformable ring being deformed against its elastic return force from its passage configuration to its immobilization configuration by centripetal radial movement of the sector carrying the axial abutment.

9. The part according to claim 8, in which the syringe support is movable relative to the end sleeve between:
    a position awaiting the injection device in which the deformable ring is in its passage configuration, and an active position of the injection device in which the deformable ring is in its configuration for the axial immobilization of the injection syringe in the syringe support, the at least one radial projection of control of the deformable ring cooperating, from the waiting position to the active position of the injection device, with the complementary surface of the end sleeve, the complementary surface forming a ramp causing the centripetal radial movement of the sector carrying the axial abutment toward the configuration for immobilization of the deformable ring.

10. The part according to claim 1, in which the deformable ring is essentially made of polymer material.

11. An injection device comprising interconnected distal part and proximal part, wherein the distal part comprises the part as claimed in claim 1.

12. The part according to claim 1, in which two diametrically opposite sectors of the deformable ring each include an axial abutment intended to cooperate with a distal shoulder of the injection syringe when the deformable ring is in the axial immobilization configuration, the deformable ring being deformed axially between its immobilization and passage configurations by radial movement of the sector carrying the axial abutment.

13. The part according to claim 12, in which the deformable ring comprises two diametrically opposite radial projections of control carried by the sector carrying the axial abutment, the two diametrically opposite radial projections of control being intended to cooperate with a complementary surface integral with the end sleeve according to the configuration to be imposed on the deformable ring.

14. The part according to claim 2, in which the deformable ring is urged elastically toward its immobilization configuration, the deformable ring being deformed against its elastic return force from its immobilization configuration to its passage configuration by centrifugal radial movement of the sector carrying the axial abutment.

15. The part according to claim 2, in which the deformable ring is urged elastically toward its passage configuration, the deformable ring being deformed against its elastic return force from its passage configuration to its immobilization configuration by centripetal radial movement of the sector carrying the axial abutment.

* * * * *